(12) United States Patent
Vess (10) Patent No.: US 9,433,532 B2
(45) Date of Patent: Sep. 6, 2016

(54) TUBELESS COMPRESSION DEVICE (71) Applicant: Covidien LP, Mansfield, MA (US)

(72) Inventor: Mark A. Vess, Hanson, MA (US)

(73) Assignee: Covidien LP, Mansfield, MA (US)

( * ) Notice: Subject to any disclaimer, the term of this patent is extended or adjusted under 35 U.S.C. 154(b) by 356 days.

(21) Appl. No.: 13/685,786

(22) Filed: Nov. 27, 2012

(65) Prior Publication Data

US 2013/0331752 A1   Dec. 12, 2013

Related U.S. Application Data (63) Continuation of application No. 12/241,936, filed on Sep. 30, 2008, now Pat. No. 8,535,253.

(51) Int. Cl.
*A61F 5/00* (2006.01)
*A61F 13/00* (2006.01)
*A61H 9/00* (2006.01)

(52) U.S. Cl.
CPC .............. *A61F 13/00* (2013.01); *A61H 9/0092* (2013.01); *A61H 2201/165* (2013.01); *A61H 2205/106* (2013.01)

(58) Field of Classification Search
CPC . A61F 5/05846; A61F 13/00; A61H 9/0092; A61H 2205/106; A61H 15/0078; A61H 2205/12
USPC ............ 602/13; 601/148–152; 141/114, 383, 141/386; 137/15.09, 15.08
See application file for complete search history.

(56) References Cited

U.S. PATENT DOCUMENTS

| 1,147,560 | A | | 7/1915 | Shurtleff |
| 1,928,992 | A | | 10/1933 | Clark et al. |
| 2,528,843 | A | | 11/1950 | Poor |
| 2,660,174 | A | | 11/1953 | Saemann |
| 3,119,125 | A | | 1/1964 | Hayes |
| 3,288,132 | A | * | 11/1966 | Meredith ...................... 601/152 |
| 3,292,613 | A | | 12/1966 | MacLeod |
| 3,396,721 | A | | 8/1968 | Menacacci |
| 3,635,216 | A | | 1/1972 | Curtis |

(Continued)

FOREIGN PATENT DOCUMENTS

| DE | 195 24 380 C2 | 10/1997 |
| DE | 198 46 922 A1 | 4/2000 |

(Continued)

OTHER PUBLICATIONS

Notification of Reason(s) for Refusal mailed Aug. 6, 2013 in corresponding Japanese Application No. 2009-225612. English language translation, 5 pages.

(Continued)

*Primary Examiner* — Kim M Lewis (57) ABSTRACT

A compression device for applying compression to a body part of a wearer has an inflatable bladder defined by first and second bladder layers and a bladder sealing line securing the first and second bladder layers to one another. A conduit is defined by spaced apart, generally opposing conduit sealing lines securing the first and second bladder layers to one another and portions of the first and second bladder layers between the conduit lines. The conduit is fluidly connected to the inflatable bladder for delivering pressurized air to the inflatable bladder. Tubing is not needed for connection to the compression device.

12 Claims, 7 Drawing Sheets

(56) References Cited

U.S. PATENT DOCUMENTS

| | | |
|---|---|---|
| 3,699,945 A | 10/1972 | Hanafin |
| 3,762,402 A | 10/1973 | Abramovitz |
| 3,825,008 A | 7/1974 | Shook |
| 3,826,249 A | 7/1974 | Lee et al. |
| 3,828,201 A | 8/1974 | Allen, Sr. |
| 3,862,629 A | 1/1975 | Rotta |
| 3,892,229 A | 7/1975 | Taylor et al. |
| 3,908,642 A | 9/1975 | Vinmont |
| 3,982,531 A | 9/1976 | Shaffer |
| 3,993,053 A | 11/1976 | Grossan |
| 4,039,039 A | 8/1977 | Gottfried |
| 4,091,804 A | 5/1978 | Hasty |
| 4,122,587 A | 10/1978 | Weiss et al. |
| 4,153,050 A | 5/1979 | Bishop et al. |
| 4,215,679 A | 8/1980 | Rustin |
| 4,228,793 A | 10/1980 | Ramey |
| 4,244,688 A | 1/1981 | Kurz |
| 4,308,861 A | 1/1982 | Kelly |
| 4,308,862 A | 1/1982 | Kalmar |
| 4,311,135 A | 1/1982 | Brueckner et al. |
| 4,372,297 A | 2/1983 | Perlin |
| D269,905 S | 7/1983 | Tamm |
| 4,402,312 A | 9/1983 | Villari et al. |
| 4,524,458 A | 6/1985 | Pongrass et al. |
| 4,548,249 A | 10/1985 | Slaughterbeck |
| 4,549,540 A | 10/1985 | Caspari et al. |
| 4,557,262 A | 12/1985 | Snow |
| 4,577,626 A | 3/1986 | Marukawa et al. |
| 4,579,555 A | 4/1986 | Russo |
| 4,702,235 A | 10/1987 | Hong |
| 4,770,164 A | 9/1988 | Lach et al. |
| 4,793,328 A | 12/1988 | Kolstedt et al. |
| 4,795,148 A | 1/1989 | Rangaswamy |
| 4,804,208 A | 2/1989 | Dye |
| 4,813,935 A | 3/1989 | Haber et al. |
| 4,824,105 A | 4/1989 | Goldenberg |
| 4,848,624 A | 7/1989 | Clem |
| 4,858,596 A | 8/1989 | Kolstedt et al. |
| 4,858,599 A | 8/1989 | Halpern |
| 4,865,020 A | 9/1989 | Bullard |
| 4,898,160 A | 2/1990 | Brownlee |
| 4,898,585 A | 2/1990 | Borsanyi et al. |
| 4,979,502 A | 12/1990 | Hunt |
| 4,993,409 A | 2/1991 | Grim |
| 5,007,411 A | 4/1991 | Dye |
| 5,027,797 A | 7/1991 | Bullard |
| 5,062,414 A | 11/1991 | Grim |
| 5,074,765 A | 12/1991 | Pekar |
| 5,078,134 A | 1/1992 | Heilman et al. |
| 5,083,320 A | 1/1992 | Halstead |
| 5,103,811 A | 4/1992 | Crupi, Jr. |
| 5,113,599 A | 5/1992 | Cohen et al. |
| 5,117,812 A | 6/1992 | McWhorter |
| 5,135,469 A | 8/1992 | Castillo |
| 5,152,302 A | 10/1992 | Fareed |
| 5,158,075 A | 10/1992 | Howard |
| 5,211,160 A | 5/1993 | Talish et al. |
| 5,211,321 A | 5/1993 | Rodriguez |
| 5,245,990 A | 9/1993 | Bertinin |
| 5,263,618 A | 11/1993 | Talavera |
| 5,277,693 A | 1/1994 | McCollor et al. |
| 5,295,996 A | 3/1994 | Blair |
| 5,309,328 A | 5/1994 | Lum |
| 5,310,400 A | 5/1994 | Rogers et al. |
| 5,312,431 A | 5/1994 | McEwen |
| 5,329,640 A | 7/1994 | Hourigan |
| 5,342,285 A | 8/1994 | Dye |
| 5,372,575 A | 12/1994 | Sebastian |
| 5,383,842 A | 1/1995 | Bertini |
| 5,391,141 A | 2/1995 | Hamilton |
| 5,403,265 A | 4/1995 | Berguer et al. |
| 5,407,418 A | 4/1995 | Szpur |
| 5,431,634 A | 7/1995 | Brown |
| 5,437,615 A | 8/1995 | Pekar et al. |
| 5,472,412 A | 12/1995 | Knoth |
| 5,478,119 A | 12/1995 | Dye |
| 5,546,955 A | 8/1996 | Wilk |
| 5,556,372 A | 9/1996 | Talish et al. |
| 5,578,055 A | 11/1996 | McEwen |
| 5,584,798 A | 12/1996 | Fox |
| 5,588,954 A | 12/1996 | Ribando et al. |
| 5,621,514 A | 4/1997 | Paranto et al. |
| 5,626,556 A | 5/1997 | Tobler et al. |
| 5,657,201 A | 8/1997 | Kochis |
| 5,669,872 A | 9/1997 | Fox |
| 5,680,026 A | 10/1997 | Lueschen |
| 5,699,570 A | 12/1997 | Wilkinson et al. |
| 5,711,469 A | 1/1998 | Gormley et al. |
| 5,711,760 A | 1/1998 | Ibrahim et al. |
| 5,743,864 A | 4/1998 | Baldwin, II |
| 5,749,493 A | 5/1998 | Boone et al. |
| 5,795,312 A | 8/1998 | Dye |
| 5,827,209 A | 10/1998 | Gross |
| 5,827,243 A | 10/1998 | Palestrant |
| 5,891,065 A | 4/1999 | Cariapa et al. |
| 5,895,369 A | 4/1999 | Flower |
| 5,902,256 A | 5/1999 | Benaron |
| 5,970,519 A | 10/1999 | Weber |
| 5,971,947 A | 10/1999 | McNally et al. |
| 5,997,465 A | 12/1999 | Savage et al. |
| 6,007,559 A | 12/1999 | Arkans |
| 6,007,940 A | 12/1999 | Spotnitz |
| 6,010,471 A | 1/2000 | Ben-Noon |
| 6,080,120 A | 6/2000 | Sandman et al. |
| 6,120,469 A | 9/2000 | Bruder |
| 6,142,962 A | 11/2000 | Mollenauer et al. |
| 6,155,263 A | 12/2000 | Weaver |
| 6,174,295 B1 | 1/2001 | Cantrell et al. |
| 6,179,797 B1 | 1/2001 | Brotz |
| 6,193,678 B1 | 2/2001 | Brannon |
| 6,203,510 B1 | 3/2001 | Takeuchi et al. |
| 6,224,538 B1 | 5/2001 | Wang et al. |
| 6,228,103 B1 | 5/2001 | Grey et al. |
| 6,260,201 B1 | 7/2001 | Rankin |
| 6,290,662 B1 | 9/2001 | Morris et al. |
| 6,319,215 B1 | 11/2001 | Manor et al. |
| 6,361,512 B1 | 3/2002 | Mackay et al. |
| 6,375,633 B1 | 4/2002 | Endress et al. |
| 6,423,017 B2 | 7/2002 | Brotz |
| 6,428,492 B2 | 8/2002 | Lloyd |
| 6,428,518 B1 * | 8/2002 | Brengle et al. ............... 604/191 |
| 6,432,070 B1 | 8/2002 | Talish et al. |
| 6,478,757 B1 | 11/2002 | Barak |
| 6,494,852 B1 | 12/2002 | Barak et al. |
| 6,540,707 B1 | 4/2003 | Stark et al. |
| 6,554,785 B1 | 4/2003 | Sroufe et al. |
| 6,579,252 B2 | 6/2003 | Lloyd et al. |
| 6,589,194 B1 | 7/2003 | Calderon et al. |
| 6,620,116 B2 | 9/2003 | Lewis |
| 6,620,117 B1 | 9/2003 | Johnson et al. |
| 6,645,165 B2 | 11/2003 | Waldridge et al. |
| 6,676,614 B1 | 1/2004 | Hansen et al. |
| 6,685,661 B2 | 2/2004 | Peled |
| 6,736,785 B1 | 5/2004 | Van Brunt |
| 6,757,916 B2 | 7/2004 | Mah et al. |
| 6,846,294 B2 | 1/2005 | Rastegar et al. |
| 6,869,408 B2 | 3/2005 | Sherman et al. |
| 6,869,409 B2 | 3/2005 | Rothman et al. |
| 6,939,314 B2 | 9/2005 | Hall et al. |
| 6,941,586 B1 | 9/2005 | Weinhold |
| 6,960,159 B2 | 11/2005 | Chung et al. |
| 6,962,277 B2 | 11/2005 | Quintana et al. |
| 6,984,201 B2 | 1/2006 | Khaghani et al. |
| 6,984,215 B2 | 1/2006 | Shah et al. |
| 6,990,700 B2 | 1/2006 | Chung |
| 7,020,508 B2 | 3/2006 | Stivoric et al. |
| 7,048,703 B2 | 5/2006 | Riach |
| 7,074,177 B2 | 7/2006 | Pickett et al. |
| 7,127,762 B1 | 10/2006 | Lau |
| 7,128,257 B2 | 10/2006 | Hyatt et al. |
| 7,186,225 B2 | 3/2007 | Kelly et al. |
| 7,186,245 B1 | 3/2007 | Cheng et al. |
| 7,210,253 B2 | 5/2007 | Yu |
| 7,226,427 B2 | 6/2007 | Steen |

(56) References Cited

U.S. PATENT DOCUMENTS

| | | |
|---|---|---|
| 7,238,163 B1 | 7/2007 | Fried et al. |
| 7,270,642 B2 | 9/2007 | Ouchene et al. |
| 7,284,291 B2 | 10/2007 | Wang |
| 7,316,658 B2 | 1/2008 | Gagne |
| 7,322,947 B2 | 1/2008 | Flick et al. |
| 7,354,410 B2 | 4/2008 | Perry et al. |
| 7,354,411 B2 | 4/2008 | Perry et al. |
| 7,376,994 B2 | 5/2008 | Wu |
| 7,384,425 B2 | 6/2008 | McEwen |
| 7,435,233 B2 | 10/2008 | Baldauf et al. |
| 7,442,175 B2 | 10/2008 | Meyer et al. |
| 7,465,296 B2 | 12/2008 | Chau |
| 7,476,207 B2 | 1/2009 | Porrata et al. |
| 7,490,620 B2 * | 2/2009 | Tesluk et al. .............. 137/15.09 |
| 7,517,325 B2 | 4/2009 | Halperin |
| 7,618,384 B2 | 11/2009 | Nardi et al. |
| 7,641,623 B2 | 1/2010 | Biondo et al. |
| 7,655,049 B2 | 2/2010 | Phillips |
| 7,701,171 B2 | 4/2010 | Defant et al. |
| 7,708,706 B2 | 5/2010 | Swidler |
| 7,708,707 B2 | 5/2010 | Cook et al. |
| 7,764,488 B2 | 7/2010 | Calvarese |
| 7,771,376 B2 | 8/2010 | Roth et al. |
| 7,827,624 B1 | 11/2010 | Cole |
| 7,857,777 B2 | 12/2010 | Larson et al. |
| 7,871,387 B2 | 1/2011 | Tordella et al. |
| 7,896,823 B2 | 3/2011 | Mangrum et al. |
| 7,896,825 B2 | 3/2011 | Atkinson et al. |
| 7,909,786 B2 | 3/2011 | Bonnefin et al. |
| 7,947,003 B2 | 5/2011 | Bonnefin et al. |
| 8,075,506 B2 | 12/2011 | Linares |
| 8,100,841 B2 | 1/2012 | Rousso |
| 8,100,842 B2 | 1/2012 | Rousso |
| 8,147,417 B2 | 4/2012 | Gavriely |
| 8,157,754 B2 | 4/2012 | Weintraub et al. |
| 8,177,734 B2 | 5/2012 | Vess |
| 8,235,921 B2 | 8/2012 | Rousso et al. |
| 8,535,253 B2 * | 9/2013 | Vess .............................. 602/13 |
| 2001/0018564 A1 | 8/2001 | Manor et al. |
| 2002/0115949 A1 | 8/2002 | Kuslich et al. |
| 2002/0194747 A1 | 12/2002 | Passke et al. |
| 2003/0074711 A1 | 4/2003 | Iversen |
| 2003/0078674 A1 | 4/2003 | Phillips |
| 2004/0046739 A1 | 3/2004 | Gettemy |
| 2004/0111048 A1 | 6/2004 | Jensen et al. |
| 2004/0147859 A1 | 7/2004 | O'Keefe |
| 2004/0147888 A1 | 7/2004 | Huang et al. |
| 2004/0199090 A1 | 10/2004 | Sanders et al. |
| 2004/0260216 A1 | 12/2004 | Zicherman |
| 2005/0015026 A1 | 1/2005 | Well et al. |
| 2005/0020946 A1 | 1/2005 | Kim |
| 2005/0107725 A1 | 5/2005 | Wild et al. |
| 2005/0148909 A1 | 7/2005 | Weil et al. |
| 2005/0278817 A1 | 12/2005 | Doheny |
| 2006/0020236 A1 | 1/2006 | Ben-Nun |
| 2006/0074362 A1 | 4/2006 | Rousso et al. |
| 2006/0085047 A1 | 4/2006 | Unsworth et al. |
| 2006/0094990 A1 | 5/2006 | Kim |
| 2006/0116615 A1 | 6/2006 | Zheng et al. |
| 2006/0122546 A1 | 6/2006 | Rousso |
| 2006/0289575 A1 | 12/2006 | Chou |
| 2007/0038167 A1 | 2/2007 | Tabron et al. |
| 2007/0049852 A1 | 3/2007 | Linnane et al. |
| 2007/0055188 A1 | 3/2007 | Avni et al. |
| 2007/0135743 A1 | 6/2007 | Meyer |
| 2007/0173886 A1 | 7/2007 | Rousso et al. |
| 2007/0179416 A1 | 8/2007 | Obrien et al. |
| 2007/0219474 A1 | 9/2007 | Wen et al. |
| 2007/0249976 A1 | 10/2007 | Tucker et al. |
| 2007/0282230 A1 | 12/2007 | Valderrabano et al. |
| 2007/0299374 A1 | 12/2007 | Gesotti et al. |
| 2008/0017678 A1 | 1/2008 | Anderson et al. |
| 2008/0068519 A1 | 3/2008 | Adler et al. |
| 2008/0141428 A1 | 6/2008 | Kapah et al. |
| 2008/0183115 A1 | 7/2008 | Pierce |
| 2008/0262399 A1 | 10/2008 | Kovelman et al. |
| 2008/0319359 A1 | 12/2008 | Moomiaie-Qajar et al. |
| 2009/0198160 A1 | 8/2009 | Coyne |
| 2010/0041943 A1 | 2/2010 | Hovland et al. |
| 2010/0081977 A1 | 4/2010 | Vess |
| 2010/0114001 A1 | 5/2010 | O'Mahony |
| 2010/0122995 A1 | 5/2010 | Thomas et al. |
| 2011/0083254 A1 | 4/2011 | Trutna et al. |
| 2011/0201981 A1 | 8/2011 | Deshpande et al. |
| 2011/0288458 A1 | 11/2011 | Jones et al. |
| 2012/0065561 A1 | 3/2012 | Ballas et al. |
| 2012/0089063 A1 | 4/2012 | Olson et al. |
| 2012/0116275 A1 | 5/2012 | Pochatko |

FOREIGN PATENT DOCUMENTS

| | | |
|---|---|---|
| DE | 20310374 U1 | 9/2003 |
| EP | 1 018 329 A2 | 7/2000 |
| GB | 2 263 405 A | 7/1993 |
| GB | 2 382 988 A | 6/2003 |
| IL | 160185 | 2/2004 |
| IL | 160214 | 2/2004 |
| IL | 162373 | 6/2004 |
| IL | 164284 | 9/2004 |
| IL | 164285 | 9/2004 |
| IL | 164286 | 9/2004 |
| JP | S58-147520 U | 9/1983 |
| JP | 2005-133553 A | 5/2005 |
| JP | 2006 333983 A | 12/2006 |
| JP | 2007-175490 A | 7/2007 |
| WO | 99/11215 A1 | 3/1999 |
| WO | 00/49968 A2 | 8/2000 |
| WO | 2004/084790 A1 | 10/2004 |
| WO | 2005/072674 A1 | 8/2005 |
| WO | 2005/074376 A2 | 8/2005 |
| WO | 2005/120424 A2 | 12/2005 |
| WO | 2005/120500 A2 | 12/2005 |
| WO | 2005/122269 A2 | 12/2005 |
| WO | 2006/013375 A1 | 2/2006 |
| WO | 2007033401 A1 | 3/2007 |
| WO | 2007085828 A1 | 8/2007 |
| WO | 2008055304 A1 | 5/2008 |
| WO | 2008084225 A1 | 7/2008 |

OTHER PUBLICATIONS

European Search Report regarding related application serial No. EP 09170464.3 dated Feb. 1 2010, 6 pgs.

European Search Report regarding related application serial No. EP 09172060 dated Feb. 2, 2010 6 pgs.

Office action issued Aug. 17, 2011 in related U.S. Appl. No. 12/241,936, 12 pgs.

Response filed Nov. 4, 2011 to Office Action dated Aug. 17, 2011 regarding related U.S. Appl. No. 12/241,936, 8 pgs.

Office action issued Jan. 5, 2012 in related U.S. Appl. No. 12/241,936, 9 pgs.

Response filed Mar. 22, 2012 to Office Action dated Jun. 6, 2012 regarding related U.S. Appl. No. 12/241,936, 9 pgs.

Final Office action issued Jun. 6, 2012 in related U.S. Appl. No. 12/241,936, 11 pgs.

Response filed Aug. 22, 2012 to Final Office Action dated Jun. 6, 2012 regarding related U.S. Appl. No. 12/241,936, 8 pgs.

Japanese Application No. 2009-225612, Japanese Patent Office, Interrogatory dated Feb. 5, 2013 with English translation, 7 pages, Japan.

* cited by examiner

TUBELESS COMPRESSION DEVICE

CROSS-REFERENCE TO RELATED APPLICATIONS

The present application is a continuation application of U.S. Ser. No. 12/241,936, filed Sep. 30, 2008, the entirety of which is incorporated by reference herein.

FIELD OF THE INVENTION

The present invention generally relates to a compression device, particularly of the type used to prevent or treat medical conditions such as deep vein thrombosis.

BACKGROUND OF THE INVENTION

A major concern for immobile patients and like persons are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popiteal and tibial return, deoxygenated blood to the heart. For example, when blood circulation in these veins is retarded due to illness, injury or inactivity, there is a tendency for blood to accumulate or pool. A static pool of blood may lead to the formation of a blood clot. A major risk associated with this condition is interference with cardiovascular circulation. Most seriously, a fragment of the blood clot can break loose and migrate. A pulmonary emboli can form from the fragment potentially blocking a main pulmonary artery, which may be life threatening. The current invention can also be applied to the treatment of other conditions, such as lymphedema.

The conditions and resulting risks associated with patient immobility may be controlled or alleviated by applying intermittent pressure to a patients limb, such as, for example, a leg to assist in blood circulation. For example, sequential compression devices have been used, such as the device disclosed in U.S. Pat. No. 4,091,804 to Hasty. Sequential compression devices are typically constructed of two sheets of material secured together at the seams to define one or more fluid impervious bladders, which are connected to a source of pressure for applying sequential pressure around a patient's body parts for improving blood return to the heart. The inflatable sections are covered with a laminate to improve durability, patient comfort, and to protect against puncture As part of the compression device, the two sheets are structurally designed to withstand a changing pressure over time under repeated use. Medical tubing is used to make connection of the source of pressure to the usually several bladders of the compression device. The source of air pressure is an air compressor most often located remotely from the patient.

SUMMARY OF THE INVENTION

In one aspect, a compression device for applying compression to a body part of a wearer generally comprises a first bladder layer of air impermeable material, and a second bladder layer of air impermeable material. The first and second bladder layers are secured to one another along a bladder sealing line, and the first and second bladder layers are disposed in opposing relationship to one another such that an inflatable bladder is defined by the first and second bladder layers and the bladder sealing line. Each of a plurality of conduits is defined by spaced apart, generally opposing conduit sealing lines securing the first and second bladder layers to one another and portions of the first and second bladder layers between the conduit sealing lines. At least one of the conduits is in fluid communication with the inflatable bladder. A unitary conduit terminal is supported by the compression device and defines passages. Each conduit is in fluid communication with one of the respective passages. Each passage is releasably connectable, along an axis generally orthogonal to the first and second bladder layers, into fluid communication with an air compressor. The conduit terminal may comprise snap connector components and each snap connector component may define at least a portion of a respective passage. Each passage may have a non-uniform diameter along the axis generally orthogonal to the first and second bladder layers. The widest portion of each passage may be defined within the unitary conduit terminal, away from any surface of the unitary conduit terminal. A portion of each passage may define a bulbous shape in a portion of the passage releasably connectable to the air compressor unit. Each passage may prevent movement of the air compressor unit in a direction parallel to the first and second bladder layers when each passage is releasably connected to the air compressor unit. The first and second bladder layers and the bladder sealing line may define a plurality of inflatable bladders and each inflatable bladder is in fluid communication with a respective one of the passages. The unitary conduit terminal may be lateral to the inflatable bladder when the compression device is disposed about the body part of the wearer. At least one of the first and second bladder layers may be sealingly joined to the conduit terminal at a respective one of the passages. The passages may be asymmetrically disposed within the unitary conduit terminal in a direction parallel to the first and second bladder layers.

In another aspect, a compression device for applying compression to a body part of a wearer generally comprises a first bladder layer of air impermeable material, and a second bladder layer of air impermeable material. The first and second bladder layers are secured to one another along a bladder sealing line. The first and second bladder layers are disposed in opposing relationship to one another such that an inflatable bladder is defined by the first and second bladder layers and the bladder sealing line. Each of a plurality of conduits is defined by spaced apart, generally opposing conduit sealing lines securing the first and second bladder layers to one another and portions of the first and second bladder layers between the conduit sealing lines. At least one of the conduits are in fluid communication with the inflatable bladder. A unitary conduit terminal is supported by the compression device and defines passages. Each conduit is in fluid communication with one of the respective passages. The unitary conduit terminal is mountable to a portable air compressor at a direct mechanical coupling defining a portion of a fluid communication path between the portable air compressor and the conduits. The direct mechanical coupling may be a plurality of receptacles defined in the unitary conduit terminal. Each receptacle is in fluid communication with a respective one of the conduits. The direct mechanical coupling may define a portion of the fluid communication path along an axis generally orthogonal to the first and second bladder layers The direct mechanical coupling may comprise snap connector components. Each snap connector component defines at least a portion of the fluid communication path.

In another aspect, a compression device for applying compression to a body part of a wearer generally comprises a first bladder layer integrally formed as a one-piece sheet of air impermeable material, and a second bladder layer integrally formed as a one-piece sheet of air impermeable material. The first and second bladder layers are disposed in opposing relationship to one another. An inflatable bladder is defined by the first and second bladder layers and a bladder sealing line secures the first and second bladder layers to one another. Each of a plurality of conduits is defined by spaced apart, generally opposing conduit sealing lines securing the first and second bladder layers to one another and portions of the first and second bladder layers between the conduit sealing lines. At least one of the conduits is fluidly connected to the inflatable bladder for delivering pressurized air to the inflatable bladder. A unitary conduit terminal supported by the compression device and having passages therein. For each conduit at least one of the first and second bladder layers is sealingly joined to the conduit terminal at a respective one of the passages to form a fluid-tight connection between the conduit terminal and the conduit whereby the passage and conduit are in fluid communication. The conduit terminal is adapted to simultaneously mount and fluidly connect a portable air compressor unit to the compression device to deliver pressurized air from the air compressor unit to the inflatable bladder.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
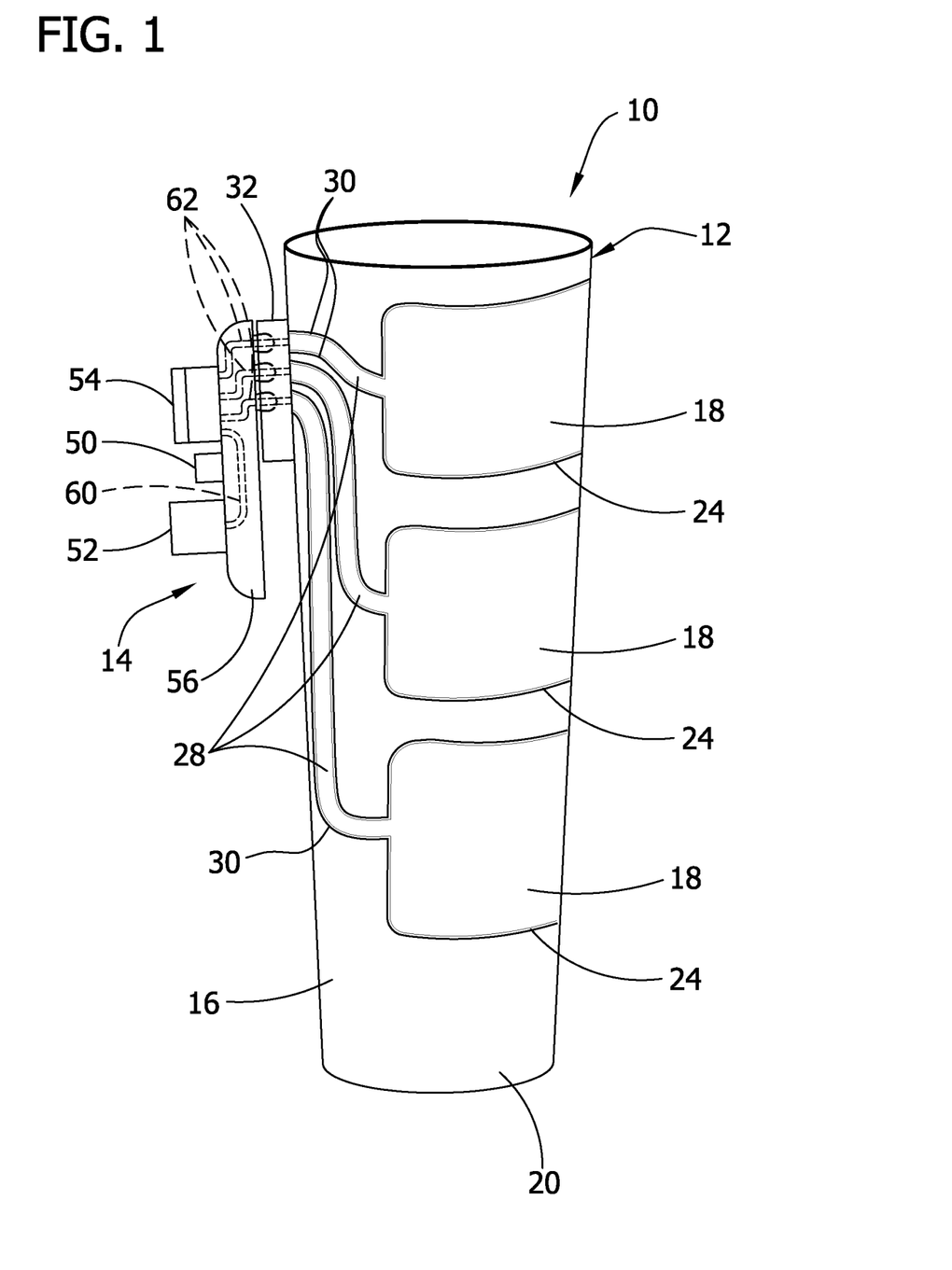
FIG. 1 is a perspective of a compression device assembly in a closed, wrapped configuration.

Referring now to the drawings and in particular to FIG. 1, a compression device assembly for applying compression therapy to a body part of a wearer is generally indicated 10. The compression device assembly includes a compression device, generally indicated at 12, and a portable controller unit, generally indicated at 14, mounted on the compression device.

Figure 2:
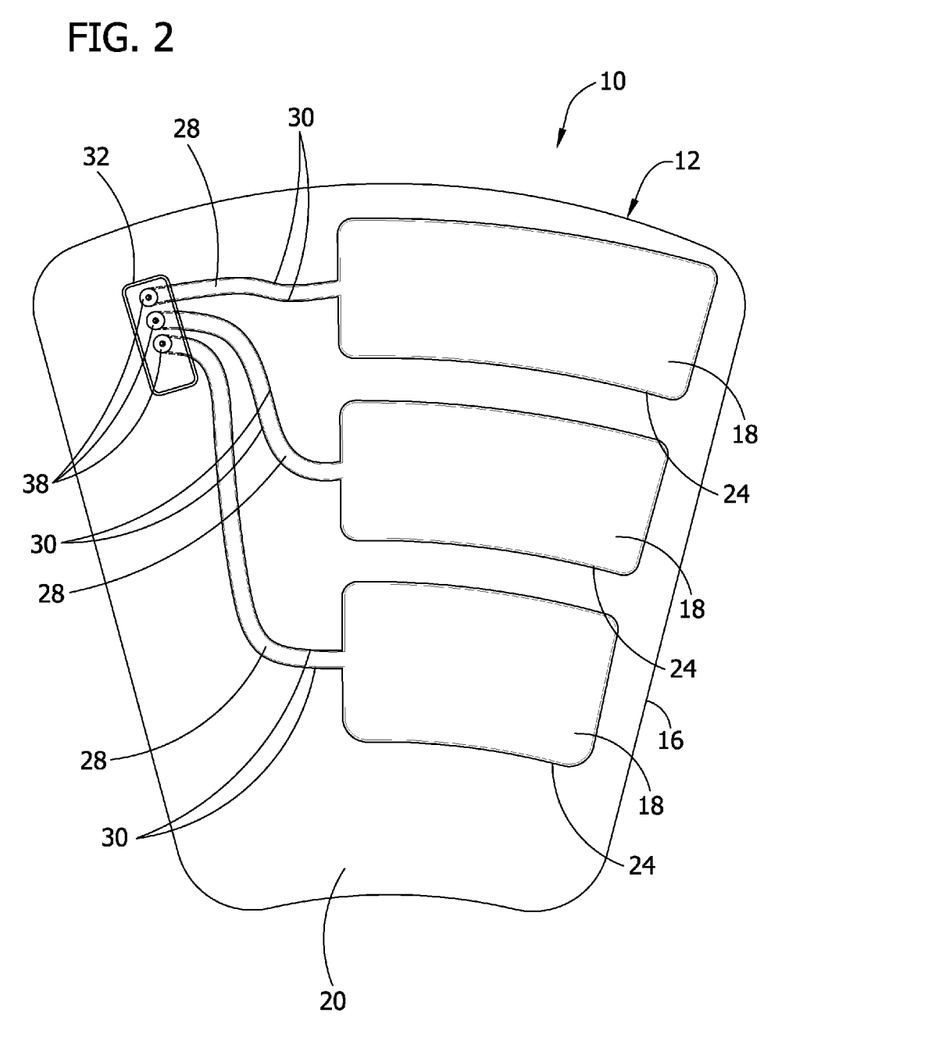
FIG. 2 is a plan view of a compression device of the compression device assembly in an open, unwrapped configuration.
Figure 3:
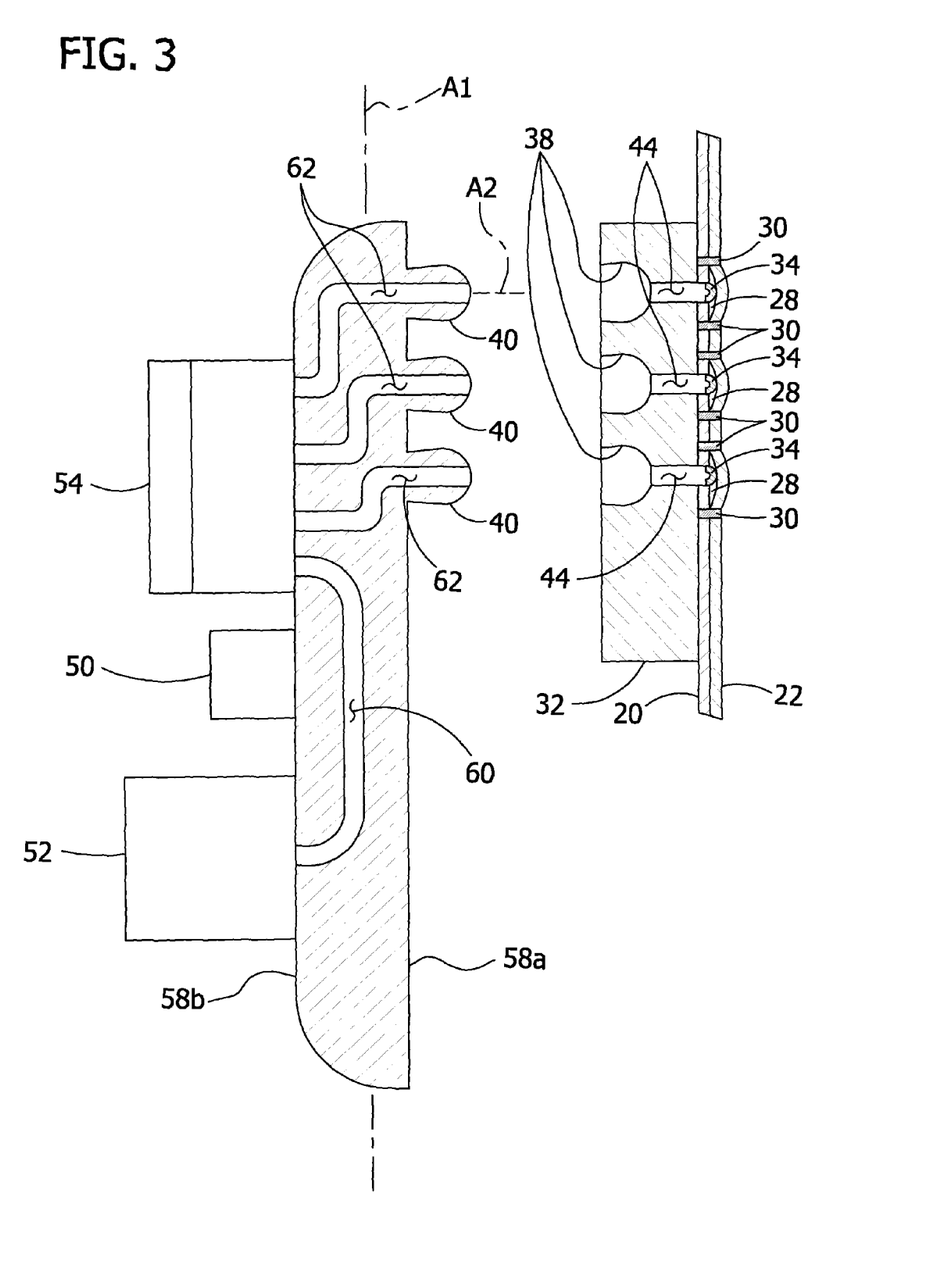
FIG. 3 is an enlarged, fragmentary section of the compression device assembly showing a portable controller unit exploded from a mount.

Referring to FIGS. 1-3, the compression device 12 of the illustrated embodiment is sized and shaped to be wrapped around a leg of a wearer. The compression device 12 includes an inflatable member 16 having three spaced apart inflatable bladders 18. The number and/or configuration of bladders may be other than shown in the illustrated embodiment. The inflatable member 16 comprises opposing inner and outer bladder layers 20, 22, respectively, secured to one another along upper, intermediate and lower bladder sealing lines 24. As used herein, the terms "inner" and "outer" refer to relative positions with respect to the wearer's leg when the device 12 is wrapped around the leg. The sealing lines 24 together with portions of the bladder layers 20, 22 within the perimeters of the lines define respective inflatable bladders 18 that are capable of retaining pressurized air. In one embodiment, each bladder layer 20, 22 is integrally formed as a single sheet of material. For example, each bladder layer 20, 22 may be formed from a single sheet of air impermeable material, such as PVC, or may be a laminated material. Further, the bladder layers 20, 22 may be welded to one another along the bladder sealing lines 24, although other ways of forming the bladder lines and the inflatable bladders are within the scope of the invention. Although not illustrated, the compression device 12 may include an inner layer or liner for contacting the skin of the wearer and an outer layer forming the exterior surface of the device. Other configurations are within the scope of the present invention.

Referring to FIGS. 1-6, conduits 28 in fluid communication with the respective inflatable bladders 18 extend from the inflatable bladders to a mount 32 (broadly, "a conduit terminal") on which the portable controller unit 14 (or "air compressor unit") is mounted, as will explained in detail below. The conduits 28 are used to deliver pressurized air from the controller unit 14 to the inflatable bladders 18 during use. Each conduit 28 is formed by a pair of spaced apart, generally opposing conduit sealing lines 30 that secure the bladder layers 20, 22 to one another. Each pair of conduit sealing lines 30 and portions of the bladder layers 20, 22 between the pair of lines define one of the conduits 28. As with the bladder sealing lines 24, the bladder layers 20, 22 may be welded to one another along the conduit sealing lines 30. Further, as in the illustrated embodiment, each bladder 18 and associated conduit 28 may be formed by a single, continuous line. For example and without being limiting, a single welding operation may form a continuous sealing line that includes the bladder sealing line 24 and the pair of conduit sealing lines 30 of one of the bladders 18 and its associated conduit 28.

Referring to FIGS. 3-6, a spacer 34 is received in each conduit 28 for maintaining the conduit open along its length so that the conduit remains in fluid communication with the controller unit 14 during use. Each spacer 34 is generally elongate and generally flexible along its length so that the spacer is able to conform to the path of the conduit 28. As shown best in FIG. 5, each spacer 34 has a generally U-shaped cross section and a height extending between the opposing bladder layers 20, 22 in the conduit. Each spacer 34 is substantially incompressible along its height, or at least will not completely collapse under normal conditions. Through this configuration, the conduits 28 remain open and the bladders 18 remain in fluid communication with the controller unit 14 despite any compressive forces being applied to the device 12 (e.g., the weight of the wearer's leg) that may close or otherwise impede fluid flow between the controller unit and one or more of the inflatable bladders. In one example, each spacer 34 is constructed of PVC or silicone, including extrudable silicone, and may be formed by extrusion or from stock.

Referring to FIGS. 1-3A, the mount 32 on which the portable controller unit 14 is mounted is secured to an exterior surface of the outer bladder layer 20. The mount 32 includes internal female connector components 38 for receiving mateable male connector components 40 of the portable controller unit 14 to releasably mount the controller unit on the compression device 12. It is understood that the mount 32 may include male connection components for being received in mateable female connector components of the portable controller unit 14 within the scope of the invention. In the illustrated embodiment, the male connection components 40 are releasably retained in the female connection components 38 by snap-fit engagement. The male connector components 40 have a slightly bulbous shape and the female connector components 38 ("receptacles") have a corresponding shape. The widest part of the male connector component 40 is wider than a mouth of the female connector component 38 so that the male component and/or female component are deformed as the male component enters the female connector component. Once the male connector component 40 is inserted far enough into the female connector component 38, it reaches a wider portion of the female connector component and "snaps" back toward its original shape. It will be appreciated that the connector components 38, 40 thereafter resist separation. However, upon application of sufficient force, the connector components 38, 40 can be disconnected. Other ways of releasably mounting the portable controller unit 14 on the compression device 12, including mateable snap-fit components, are within the scope of the invention.

Figure 3A:
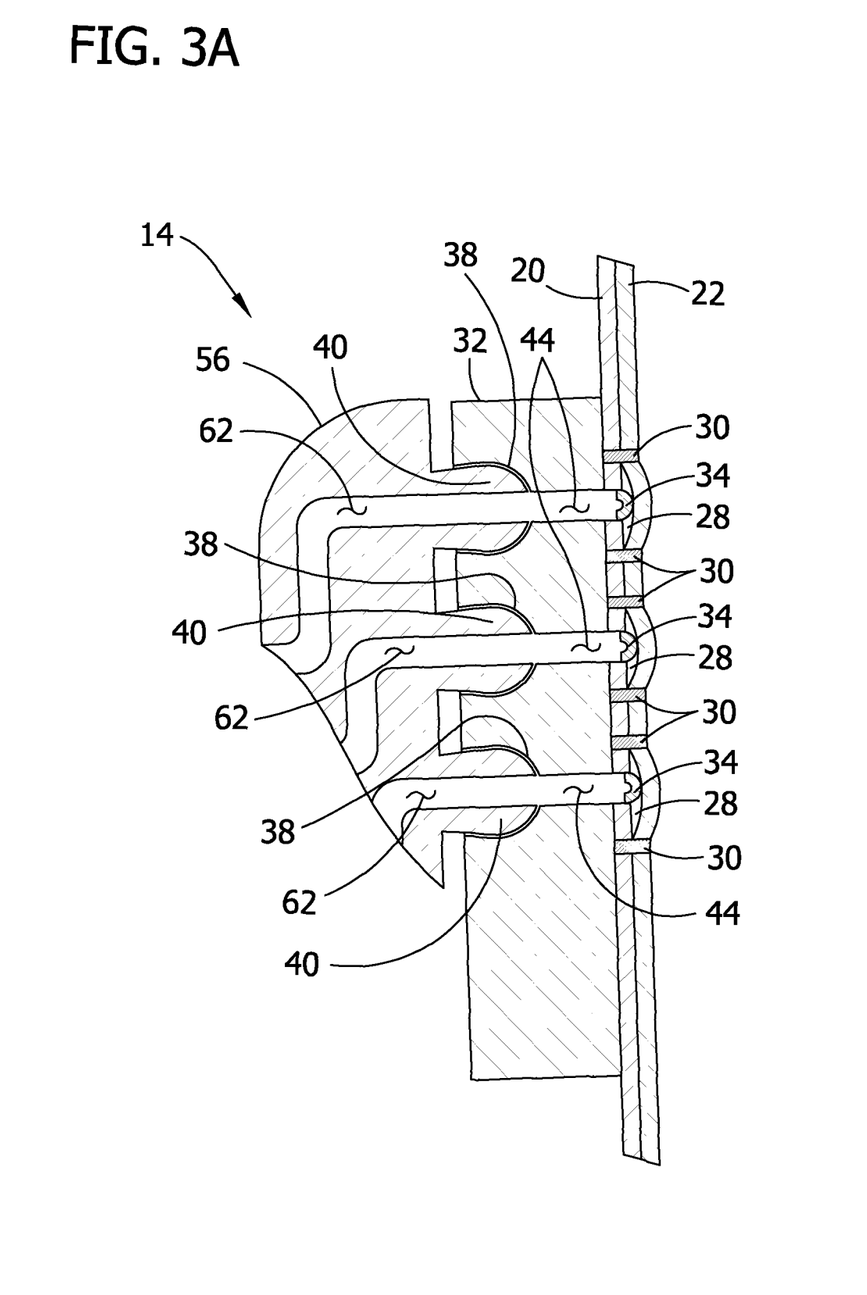
FIG. 3A is an enlarged, fragmentary view of FIG. 3 with the portable controller unit connected to the mount.
Figure 4:
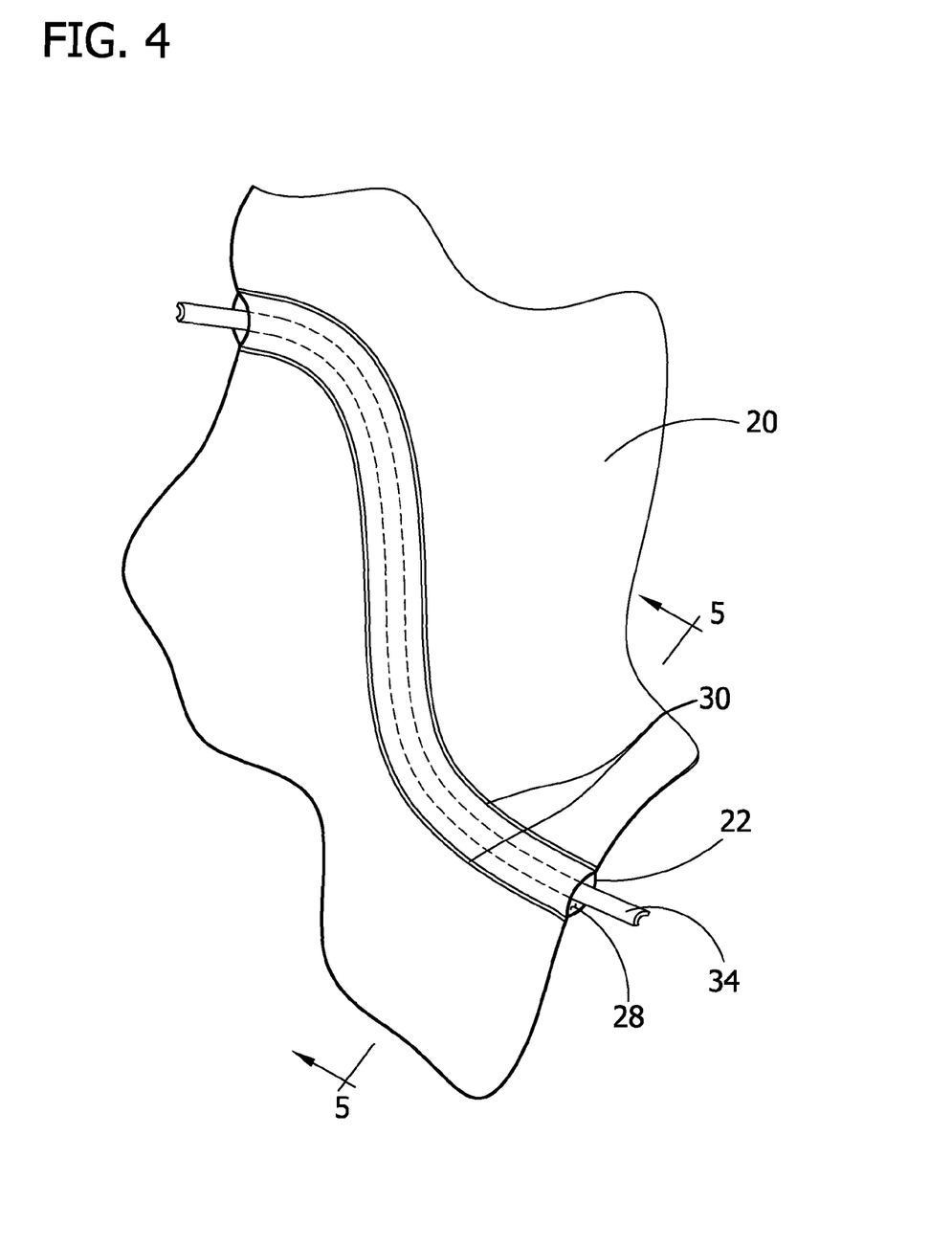
FIG. 4 is an enlarged, fragmentary view of a portion of the compression device.
Figure 5:
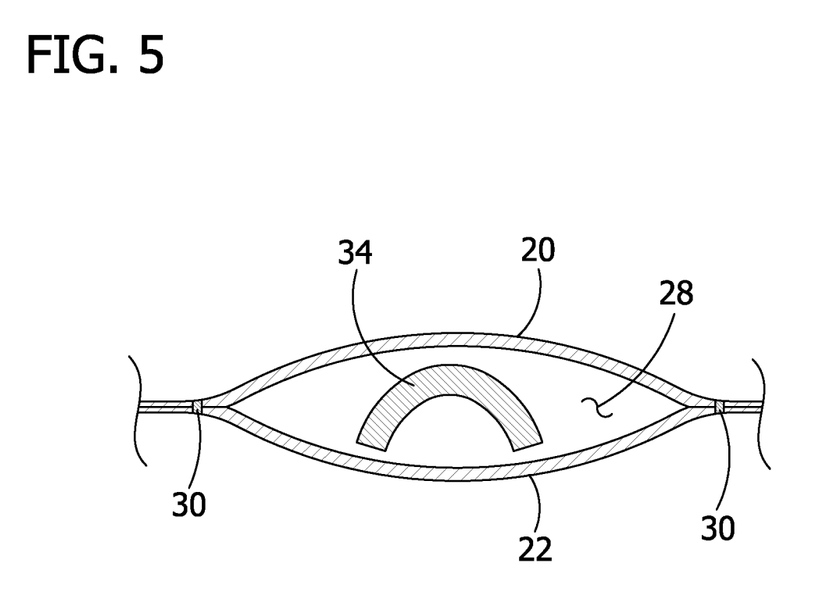
FIG. 5 is an enlarged section of the compression device taken along the line 5-5 in FIG. 4.
Figure 6:
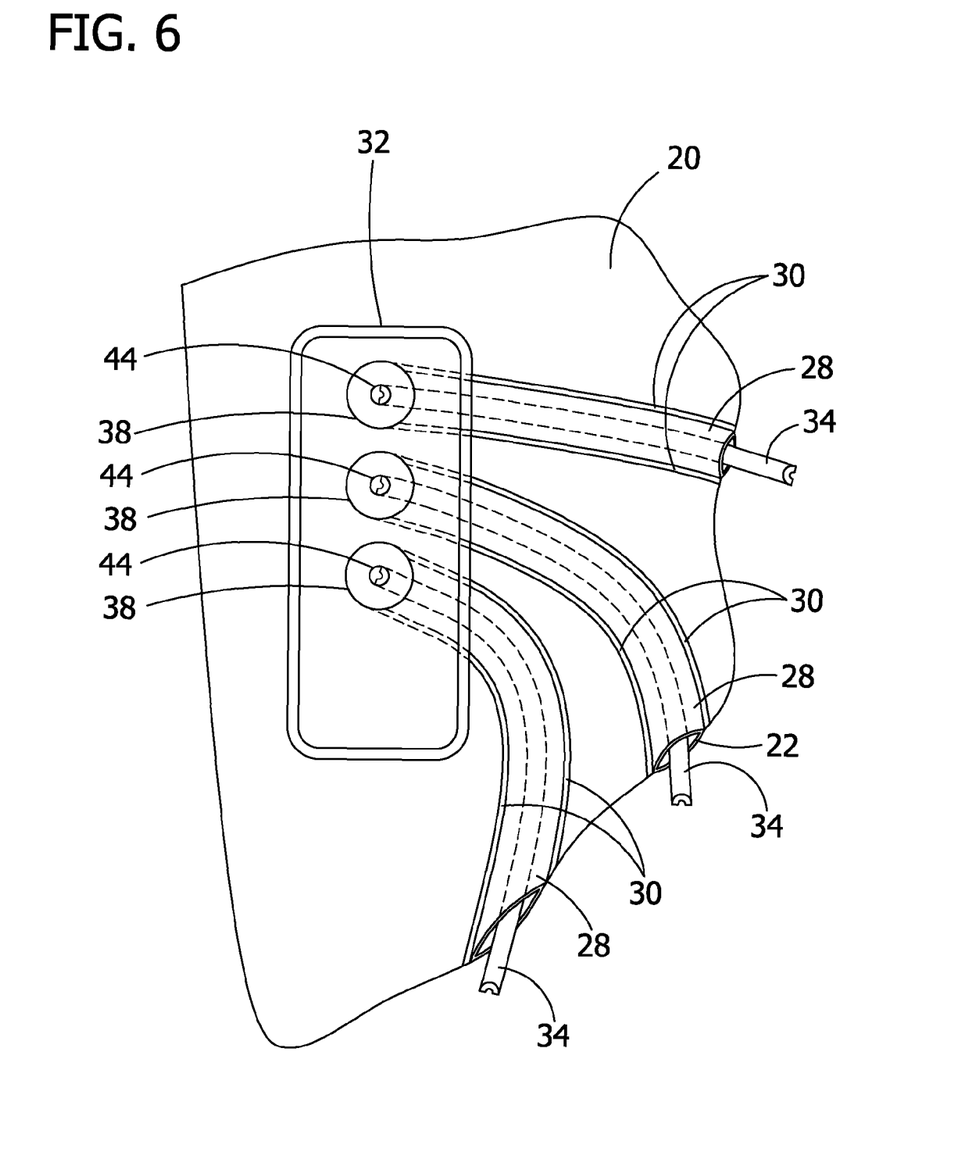
FIG. 6 is an enlarged, fragmentary view of the compression device.

Referring to FIGS. 3 and 3A, each female connector component 38 of the mount 32 is fluidly connected to one of the conduits 28 via an inlet passage 44 inside the mount. In one example, the mount 32, including the female connector components 38 and the inlet passages 44, is molded as a one-piece unit. Other ways of forming the mount 32 are within the scope of the invention. The mount 32 is secured to the inner and outer bladder layers 20, 22 by heat welding (e.g., radiofrequency (RF) welding), adhesive, mechanical connectors or in other ways so that the inlet passages 44 in the mount are in sealed, fluid communication with the respective bladder conduits 28. For example and without being limiting, in one method the mount 32 is placed in an RF welding die together with a sheet that will become the inner bladder layer 20, and the sheet is welded to the mount 32 around the inlet passage 44. The outer bladder layer 22 and spacers 34 (one for each conduit 28 to be formed) are next placed in the welding die. A second weld is formed connecting the inner and outer bladder layers 20, 22 together and connecting both layers to the mount 32 from each inlet passage 44 to the periphery of the mount, thereby forming a small section of the conduit 28. A U-shaped die member (not shown) is used for this procedure so that the small section of the conduit 28 is left open at the periphery of the mount 32. A third welding step joins the inner and outer bladder layers 20, 22 together to form the remainder of each conduit 28, as well as the bladders 18. The spacers 34 are encapsulated in the conduits 28 in the third welding step. Two different welding steps are used to form the conduits 28 because of the difference in thickness of material when the mount 32 is present in the weld line, versus when the mount is not part of the weld. However it is envisioned that the conduits 28 could be formed in a single step with a properly tuned weld die.

Referring to FIG. 1, the portable controller unit 14 includes a controller 50 electrically connected to an air compressor 52 and a valve mechanism 54. Each of the componets 50, 52, 54 is mounted on a manifold base 56 (broadly, a base). As explained below, the male connection components 40 extend outward from the manifold base 56. More specifically, the male connection components 40 extend outward from a first face 58a (FIG. 3) of the base 56 and the controller 50, air compressor 52 and valve mechanism 54 are mounted on an opposite second face 58b (FIG. 3) of the base. In the illustrated embodiment, a longitudinal axis A1 of the base 56 is generally orthogonal to axes A2 (only one is illustrated) of the connection components 40. The controller 50 may be a microprocessor that communicates with the air compressor 52 and the valve mechanism 54 during operation. The valve mechanism 54 may comprise a plurality of valves (e.g., solenoid valves) that are controlled by the microprocessor. Although not illustrated in the drawings, the controller unit may include a rechargeable, portable power source, such as a battery for supplying power to the controller 50, the air compressor, 52 and the valve mechanism 54. The operation of the portable controller unit 14 may operate generally in the same manner as taught in the art.

Referring to FIGS. 1 and 3, the manifold base 56 includes a single internal inlet plenum 60 and a plurality of internal outlet plenums 62 extending through the male connector components 40. The inlet plenum 60 fluidly connects the air compressor 52 and the valve mechanism 54. The inlet plenum 60 extends from the second face 58b of the manifold base 56 at a first location to a second location on the second face. The air compressor 52 is mounted on the second face 58b of the base 56 in fluid communication with the inlet plenum 60 at the first location. The outlet plenums 62 fluidly connect the valve mechanism 54 and the male connector components 40. The outlet plenums 62 extend through the second face 58b of the base 56 at third location and extend axially through the male connector components 40 to fluidly connect the valve mechanism 54 to the respective conduits 28 and the respective bladders 18. The valve mechanism 54 is mounted on the second face 58b of the base 56 in fluid communication with both the inlet plenum 62 at the second location and the outlet plenums 62 at the third locations. In one example, the manifold base 56, including the inlet plenum 60, the outlet plenums 62 and the male connector components 40, is molded as a single, integral unit. For example, the base 56 and the male components 40 may be formed from a resilient polymeric material. It is understood that the base 56 may be formed in other ways without departing from the scope of the present invention. The portable controller unit 14 may also include a cover (not shown) detachably secured to the manifold base 56 to enclose the controller 50, the air compressor 52 and the valve mechanism 54.

In an exemplary use, the compression device assembly 10 is wrapped around a limb, e.g., a leg, of a patient. Mateable fasteners, such as hook and loop fasteners (not shown), that are adjacent to opposite lateral edges of the compression device 12 may be used to releasably secure the compression device to the wearer's limb, as is generally known in the art. Before or after the compression device 12 is secured to the wearer's limb, the portable controller unit 14 is mounted on the device by inserting the male connection components 40 into the respective female connection components 38 in the mount 32. As explained above, the male connection components 38 are retained in the female connection components by snap-fit engagement. With the controller unit 14 mounted on the device 12, the controller unit is in fluid communication with the inflatable bladders 18. The controller 50 can be activated to begin compression therapy, whereby the air compressor 52 delivers pressurized air via the inlet plenum 60 in the manifold base 56 to the valve mechanism 54, which diverts the air into one of the three outlet plenums 62 and into the appropriate bladder 18 via one of the conduits 28. The portable controller unit 14 can be detached from the compression 12 by simply pulling the base 56 away from the mount 32 so that the male connection components 40 disengage the female connection components 38 in the mount 32. It will be appreciated that separate tubing for delivering air is eliminated in the illustrated embodiment. It is envisioned that the compression device 12 may be disposable and constructed for one-time use. Thus, the portable controller unit 14 having a rechargeable power source can be reused and mounted on another compression device 12 of the same type.

When introducing elements of the present invention or the preferred embodiments(s) thereof, the articles "a", "an" "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description shown in the accompanying drawings shall be interpreted as illustrative and not in a limiting sense.

What is claimed is:

1. A compression device for applying compression to a body part of a wearer, the compression device comprising:
   a first bladder layer of air impermeable material;
   a second bladder layer of air impermeable material, the first and second bladder layers secured to one another along a bladder sealing line, and the first and second bladder layers disposed in opposing relationship to one another such that an inflatable bladder is defined by the first and second bladder layers and the bladder sealing line;
   a plurality of conduits, each conduit defined by spaced apart, generally opposing conduit sealing lines securing the first and second bladder layers to one another and portions of the first mand second bladder layers between the conduit sealing lines, at least one of the conduits in fluid communication with the inflatable bladder;
   a unitary conduit terminal supported by the compression device along a first surface of the unitary conduit terminal and defining passages in the unitary conduit terminal, each conduit in fluid communication with a respective one of the passages, wherein each passage is releasably connectable, along an axis generally orthogonal to the first and second bladder layers, into fluid communication with an air compressor along a second surface of the unitary conduit terminal;
   wherein each passage has a non-uniform diameter along the axis generally orthogonal to the first and second bladder layers, each passage including a narrow portion extending from the first surface of the unitary conduit terminal and a wider portion extending from the narrow portion to the second surface of the unitary conduit terminal opposite the first surface, and wherein the wider portion of each passage defines a bulbous shape tapering in width toward the second surface of the unitary conduit terminal and releasably connectable to the air compressor.

2. The compression device of claim 1, wherein the conduit terminal comprises snap connector components and each snap connector component defines at least a portion of a respective passage.

3. The compression device of claim 1, wherein each passage prevents movement of the air compressor in a direction parallel to the first and second bladder layers when each passage is releasably connected to the air compressor.

4. The compression device of claim 1, wherein the first and second bladder layers and the bladder sealing line define a plurality of inflatable bladders and each inflatable bladder is in fluid communication with a respective one of the passages.

5. The compression device of claim 1, wherein the unitary conduit terminal is lateral to the inflatable bladder when the compression device is disposed about the body part of the wearer.

6. The compression device of claim 1, wherein at least one of the first and second bladder layers is sealingly joined directly to the conduit terminal at a respective one of the passages.

7. The compression device of claim 1, wherein the passages are asymmetrically disposed within the unitary conduit terminal in a direction parallel to the first and second bladder layers.

8. A compression device for applying compression to a body part of a wearer, the compression device comprising:
   a first bladder layer of air impermeable material;
   a second bladder layer of air impermeable material, the first and second bladder layers secured to one another along a bladder sealing line, and the first and second bladder layers disposed in opposing relationship to one another such that an inflatable bladder is defined by the first and second bladder layers and the bladder sealing line;
   a plurality of conduits, each conduit defined by spaced apart, generally opposing conduit sealing lines securing the first and second bladder layers to one another and portions of the first and second bladder layers between the conduit sealing lines, at least one of the conduits in fluid communication with the inflatable bladder;
   a unitary conduit terminal supported by the compression device along a first surface of the unitary conduit terminal and defining passages in the unitary conduit terminal, each conduit in fluid communication with a respective one of the passage, wherein the unitary conduit terminal is mountable to a portable air compressor at a direct mechanical coupling along a second surface of the unitary conduit terminal defining a portion of a fluid communication path between the portable air compressor and the conduits;
   wherein each passage has a non-uniform diameter along an axis generally orthogonal to the first and second bladder layers, each passage including a narrow portion extending from the first surface of the unitary conduit terminal and a wider portion extending from the narrow portion to the second surface of the unitary conduit terminal opposite the first surface, and wherein the wider portion of each passage defines a bulbous shape tapering in width toward the second surface of the unitary conduit terminal and releasably connectable to the air compressor.

9. The compression device of claim 8, wherein the direct mechanical coupling is a plurality of receptacles defined in the unitary conduit terminal, each receptacle in fluid communication with a respective one of the conduits.

10. The compression device of claim 8, wherein the direct mechanical coupling defines a portion of the fluid communication path along an axis generally orthogonal to the first and second bladder layers.

11. The compression device of claim 8, wherein the direct mechanical coupling comprises snap connector components, each snap connector component defining at least a portion of the fluid communication path.

12. A compression device for applying compression to a body part of a wearer, the compression device comprising:
- a first bladder layer integrally formed as a one-piece sheet of air impermeable material;
- a second bladder layer integrally formed as a one-piece sheet of air impermeable material, the first and second bladder layers being disposed in opposing relationship to one another;
- an inflatable bladder defined by the first and second bladder layers and a bladder sealing line securing the first and second bladder layers to one another;
- a plurality of conduits, each conduit being defined by spaced apart, generally opposing conduit sealing lines securing the first and second bladder layers to one another and portions of the first and second bladder layers between the conduit sealing lines, at least one of the conduits being fluidly connected to the inflatable bladder for delivering pressurized air to the inflatable bladder;
- a unitary conduit terminal supported by the compression device along a first surface of the unitary conduit terminal and having passages therein, for each conduit at least one of the first and second bladder layers being sealingly joined to the conduit terminal at a respective one of the passages to form a fluid-tight connection between the conduit terminal and the conduit whereby the passage and conduit are in fluid communication, wherein the conduit terminal is adapted to simultaneously mount and fluidly connect a portable air compressor unit to the compression device to deliver pressurized air from the portable air compressor unit to the inflatable bladder, the conduit terminal mounting the portable air compressor unit along a second surface of the conduit terminal;
- wherein each passage has a non-uniform diameter along an axis generally orthogonal to the first and second bladder layers, each passage including a narrow portion extending from the first surface of the unitary conduit terminal and a wider portion extending from the narrow portion to the second surface of the unitary conduit terminal opposite the first surface, and wherein the wider portion of each passage defines a bulbous shape tapering in width toward the second surface of the unitary conduit terminal and releasably connectable to the portable air compressor unit.

* * * * *